(12) United States Patent
Jamello

(10) Patent No.: US 9,526,473 B2
(45) Date of Patent: Dec. 27, 2016

(54) APPARATUS AND METHOD FOR MEDICAL IMAGE SEARCHING

(71) Applicant: ACIST Medical Systems, Inc., Eden Prairie, MN (US)

(72) Inventor: Joseph A. Jamello, Saratoga, CA (US)

(73) Assignee: ACIST Medical Systems, Inc., Eden Prairie, MN (US)

(*) Notice: Subject to any disclaimer, the term of this patent is extended or adjusted under 35 U.S.C. 154(b) by 0 days.

(21) Appl. No.: 15/133,558

(22) Filed: Apr. 20, 2016

(65) Prior Publication Data

US 2016/0228089 A1   Aug. 11, 2016

Related U.S. Application Data

(62) Division of application No. 13/228,941, filed on Sep. 9, 2011, now Pat. No. 9,351,703.

(Continued)

(51) Int. Cl.
*A61B 8/14*   (2006.01)
*A61B 8/12*   (2006.01)
(Continued)

(52) U.S. Cl.
CPC .............. *A61B 8/12* (2013.01); *A61B 8/0883* (2013.01); *A61B 8/0891* (2013.01); *A61B 8/13* (2013.01);
(Continued)

(58) Field of Classification Search
CPC .. G06F 19/3481; G06F 19/345; G06F 3/0346; G06F 19/3437; G06F 19/321; G06F 19/3456
See application file for complete search history.

(56) References Cited

U.S. PATENT DOCUMENTS 7,469,381 B2   12/2008   Ording
7,479,949 B2   1/2009   Jobs et al.
(Continued)

FOREIGN PATENT DOCUMENTS

JP   06089143 A   3/1994
JP   10262964 A   10/1998
(Continued)

OTHER PUBLICATIONS

PCT International Search Report and Written Opinion for PCT Application No. PCT/US2011/051118, mailed Apr. 27, 2012, 18 pages.

(Continued)

*Primary Examiner* — Nicholas Augustine
(74) *Attorney, Agent, or Firm* — Fredrikson & Byron, P.A.

(57) ABSTRACT

An intravascular ultrasound (IVUS) imaging system and catheter with an intuitive interface for rapid operator interaction using acquired medical images. In an embodiment, an IVUS imaging system and catheter are used to acquire a sequence of a specific area of interest in the human anatomy, for example, tomographic images of a coronary artery. The IVUS imaging system displays at least one tomographic image of the area of interest. The IVUS imaging system generates and displays at least one longitudinal image, wherein the longitudinal image represents a cut-plane of the sequence of tomographic images. The IVUS imaging system further includes a touch screen, wherein the system recognizes touch movements to facilitate searching the sequence of images. Touch movements in a longitudinal direction may pan the longitudinal image in the longitudinal direction. Touch movements in the transverse direction may rotate the cut-plane of the longitudinal image.

20 Claims, 6 Drawing Sheets

Related U.S. Application Data

(60) Provisional application No. 61/381,528, filed on Sep. 10, 2010.

(51) Int. Cl.

| | | |
|---|---|---|
| *A61B 8/08* | (2006.01) | |
| *A61B 8/00* | (2006.01) | |
| *G06F 3/0488* | (2013.01) | |
| *A61B 8/13* | (2006.01) | |
| *G06F 3/0354* | (2013.01) | |
| *G06F 3/0481* | (2013.01) | |
| *G06F 3/0484* | (2013.01) | |
| *G06F 3/0485* | (2013.01) | |
| *G06T 3/60* | (2006.01) | |
| *G06T 11/00* | (2006.01) | |
| *G06T 15/00* | (2011.01) | |
| *A61B 1/00* | (2006.01) | |
| *G06F 19/00* | (2011.01) | |

(52) U.S. Cl.
CPC ............. *A61B 8/14* (2013.01); *A61B 8/463* (2013.01); *A61B 8/465* (2013.01); *A61B 8/466* (2013.01); *A61B 8/467* (2013.01); *G06F 3/03545* (2013.01); *G06F 3/0485* (2013.01); *G06F 3/04815* (2013.01); *G06F 3/04842* (2013.01); *G06F 3/04845* (2013.01); *G06F 3/04883* (2013.01); *G06T 3/60* (2013.01); *G06T 11/003* (2013.01); *G06T 15/00* (2013.01); *A61B 8/565* (2013.01); *G06F 19/321* (2013.01); *G06F 2203/04808* (2013.01); *G06T 2219/008* (2013.01)

(56) References Cited

U.S. PATENT DOCUMENTS

| | | |
|---|---|---|
| 8,457,353 B2 | 6/2013 | Reville et al. |
| 8,560,968 B1 | 10/2013 | Nair |
| 2005/0090743 A1 | 4/2005 | Kawashima et al. |
| 2006/0232563 A1 | 10/2006 | Lii et al. |
| 2006/0241465 A1 | 10/2006 | Huennekens et al. |
| 2007/0268269 A1 | 11/2007 | Chang et al. |
| 2008/0044069 A1 | 2/2008 | DuGal |
| 2008/0051657 A1 | 2/2008 | Rold |
| 2008/0122796 A1 | 5/2008 | Jobs et al. |
| 2008/0306379 A1 | 12/2008 | Ikuma et al. |
| 2009/0244033 A1 | 10/2009 | Westerman et al. |
| 2009/0276515 A1 | 11/2009 | Thomas et al. |
| 2010/0042084 A1 | 2/2010 | Nariyuki et al. |
| 2010/0079411 A1 | 4/2010 | Lee et al. |
| 2010/0171712 A1 | 7/2010 | Cieplinski et al. |
| 2010/0222671 A1 | 9/2010 | Cohen et al. |
| 2010/0281380 A1 | 11/2010 | Langmacher et al. |
| 2010/0309198 A1 | 12/2010 | Kauffmann |

FOREIGN PATENT DOCUMENTS

| | | |
|---|---|---|
| JP | 2008531200 A | 8/2008 |
| WO | 2006093776 A1 | 9/2006 |

OTHER PUBLICATIONS

Extended European Search Report for EP Application No. 11824222.1, Date of mailing: Apr. 5, 2016, 10 pages.

APPARATUS AND METHOD FOR MEDICAL IMAGE SEARCHING

CLAIM TO PRIORITY

This application is a divisional application of U.S. patent application Ser. No. 13/228,941, filed Sep. 9, 2011, entitled APPARATUS AND METHOD FOR MEDICAL IMAGE SEARCHING, which in turn claims the benefit of U.S. Provisional Patent Application No. 61/381,528, entitled APPARATUS AND METHOD FOR MEDICAL IMAGE SEARCHING, which was filed on Sep. 10, 2010 and is incorporated herein by reference in its entirety.

BACKGROUND

The subject matter disclosed herein generally relates to medical imaging systems, search methods within medical imaging systems and intravascular ultrasound (IVUS) imaging systems. In medical imaging in general, luminal structures of a living body can be visualized by using a medical imaging device that acquires a sequence of images. The sequence of images may include thousands of images about a specific part of the human anatomy. For clinical diagnosis, an operator may need to search the sequence of images to identify at least one image feature of interest. For example, an IVUS imaging system and catheter may be used by an interventional cardiologist to locate a minimum lumen area within a segment of an atherosclerotic-diseased coronary artery.

An IVUS system generally displays at least a single plane (tomographic) image of the coronary artery. The IVUS system may further display a longitudinal view of the coronary artery wherein the longitudinal view is a cut-plane of a sequence of tomographic images that are acquired as an IVUS catheter transducer is translated through the coronary artery. The image sequence may include many thousands of tomographic images depending on the imaging frame rate and translation rate of the sensor through the coronary artery.

Thus, with thousands of potential tomographic images to view, a need for a display technology that provides a more intuitive approach and rapid interaction for the operator to guide interventional cardiology procedures arises. Further, it is desirable that such a display technology reduce to time to identify at least one image feature of interest in a sequence of images.

BRIEF DESCRIPTION OF THE DRAWINGS

The foregoing aspects and many of the attendant advantages of the claims will become more readily appreciated as the same become better understood by reference to the following detailed description, when taken in conjunction with the accompanying drawings, wherein:

DETAILED DESCRIPTION

The following discussion is presented to enable a person skilled in the art to make and use the subject matter disclosed herein. The general principles described herein may be applied to embodiments and applications other than those detailed above without departing from the spirit and scope of the present detailed description. The present disclosure is not intended to be limited to the embodiments shown, but is to be accorded the widest scope consistent with the principles and features disclosed or suggested herein.

In embodiments described herein, an intravascular ultrasound (IVUS) imaging system and catheter provides an intuitive interface for rapid operator interaction with acquired medical images. The IVUS imaging system and catheter are used to acquire a sequence of a specific area of interest in the human anatomy, for example, tomographic images of a coronary artery. The IVUS imaging system displays at least one tomographic image of the area of interest. The IVUS imaging system generates and displays at least one longitudinal image, wherein the longitudinal image represents a cut-plane of the sequence of tomographic images. In the coronary artery example, the longitudinal image includes a longitudinal axis along the coronary artery axis and a transverse axis perpendicular to the coronary artery axis.

The IVUS imaging system further includes a touch screen, wherein the system recognizes touch movements to facilitate searching the sequence of images. Touch movements in the longitudinal direction of the longitudinal image may pan the longitudinal image in the longitudinal direction. Touch movements in the transverse direction of the longitudinal image may rotate the cut-plane of the longitudinal image. The IVUS imaging system further includes touch movement (heuristic) processing to preferentially pan the longitudinal image in one direction or another. These and other aspects are discussed in greater detail below with respect to the FIGs. As briefly introduced above.

Figure 1:
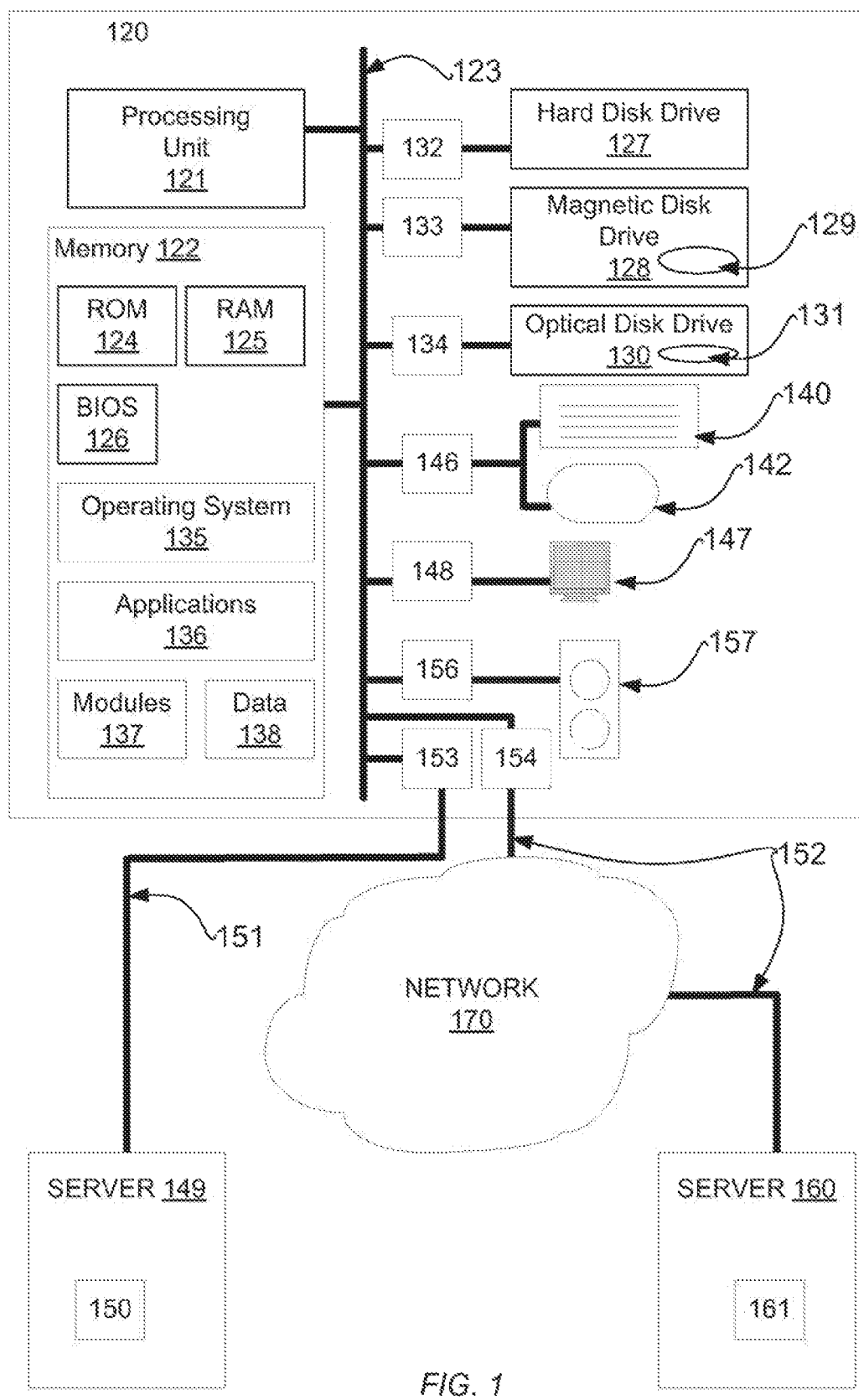
FIG. 1 shows a diagram of a suitable computing environment for practicing various aspects of a medical imaging system and method according to an embodiment of the subject matter disclosed herein.

FIG. 1 and the following discussion are intended to provide a brief, general description of a suitable computing environment in which the subject matter disclosed herein may be implemented. Although not required, aspects of a system and method for manipulating a medical image will be described in the general context of computer-executable instructions, such as program modules, being executed by a personal computer. Generally, program modules include routines, programs, objects, components, data structures, etc., that perform particular tasks or implement particular abstract data types. Such program module may be embodied in both a transitory and/or a non-transitory computer readable medium having computer-executable instructions. Moreover, those skilled in the art will appreciate that the invention may be practiced with other computer system configurations, including hand-held devices, cellular or mobile telephones, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

With reference to FIG. 1, an exemplary system for implementing the systems and methods disclosed herein includes a general purpose computing device in the form of a conventional personal computer 120, including a processing unit 121, a system memory 122, and a system bus 123 that couples various system components including the system memory to the processing unit 121. The system bus 123 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The system memory includes read only memory (ROM) 124 and random access memory (RAM) 125. A basic input/output system (BIOS) 126, containing the basic routines that help to transfer information between elements within the personal computer 120, such as during start-up, is stored in ROM 124. The personal computer 120 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of computer readable instructions, data structures, program modules and other data for the personal computer 120. Although the exemplary environment described herein employs a hard disk, a removable magnetic disk 129 and a removable optical disk 131, it should be appreciated by those skilled in the art that other types of computer-readable media which can store data that is accessible by a computer, such as magnetic cassettes, flash memory cards, digital versatile disks, Bernoulli cartridges, random access memories (RAMs), read only memories (ROM), and the like, may also be used in the exemplary operating environment.

A number of program modules may be stored on the hard disk, magnetic disk 129, optical disk 131, ROM 124 or RAM 125, including an operating system 135, one or more application programs 136, other program modules 137, and program data 138. A user may enter commands and information into the personal computer 120 through input devices such as a keyboard 140 and pointing device 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port or a universal serial bus (USB). A monitor 147 or other type of display device is also connected to the system bus 123 via an interface, such as a video adapter 148. One or more speakers 157 are also connected to the system bus 123 via an interface, such as an audio adapter 156. In addition to the monitor and speakers, personal computers typically include other peripheral output devices (not shown), such as printers.

The personal computer 120 may also operate in a networked environment using logical connections to one or more remote computers, such as remote computers 149 and 160. Each remote computer 149 or 160 may be another personal computer, a server, a router, a network PC, a peer device or other common network node, and typically includes many or all of the elements described above relative to the personal computer 120, although only a memory storage device 150 or 161 has been illustrated in FIG. 1. The logical connections depicted in FIG. 1 include a local area network (LAN) 151 and a wide area network (WAN) 152. Such networking environments are commonplace in offices, enterprise-wide computer networks, intranets and the Internet. As depicted in FIG. 1, the remote computer 149 communicates with the personal computer 120 via the local area network 151. The remote computer 160 communicates with the personal computer 120 via the wide area network 152.

When used in a LAN networking environment, the personal computer 120 is connected to the local network 151 through a network interface or adapter 153. When used in a WAN networking environment, the personal computer 120 typically includes a modem 154 or other means for establishing communications over the wide area network 152, such as the Internet. The modem 154, which may be internal or external, is connected to the system bus 123. In a networked environment, program modules depicted relative to the personal computer 120, or portions thereof, may be stored in the remote memory storage device. It will be appreciated that the network connections shown are exemplary and other means of establishing a communications link between the computers may be used.

Figure 2:
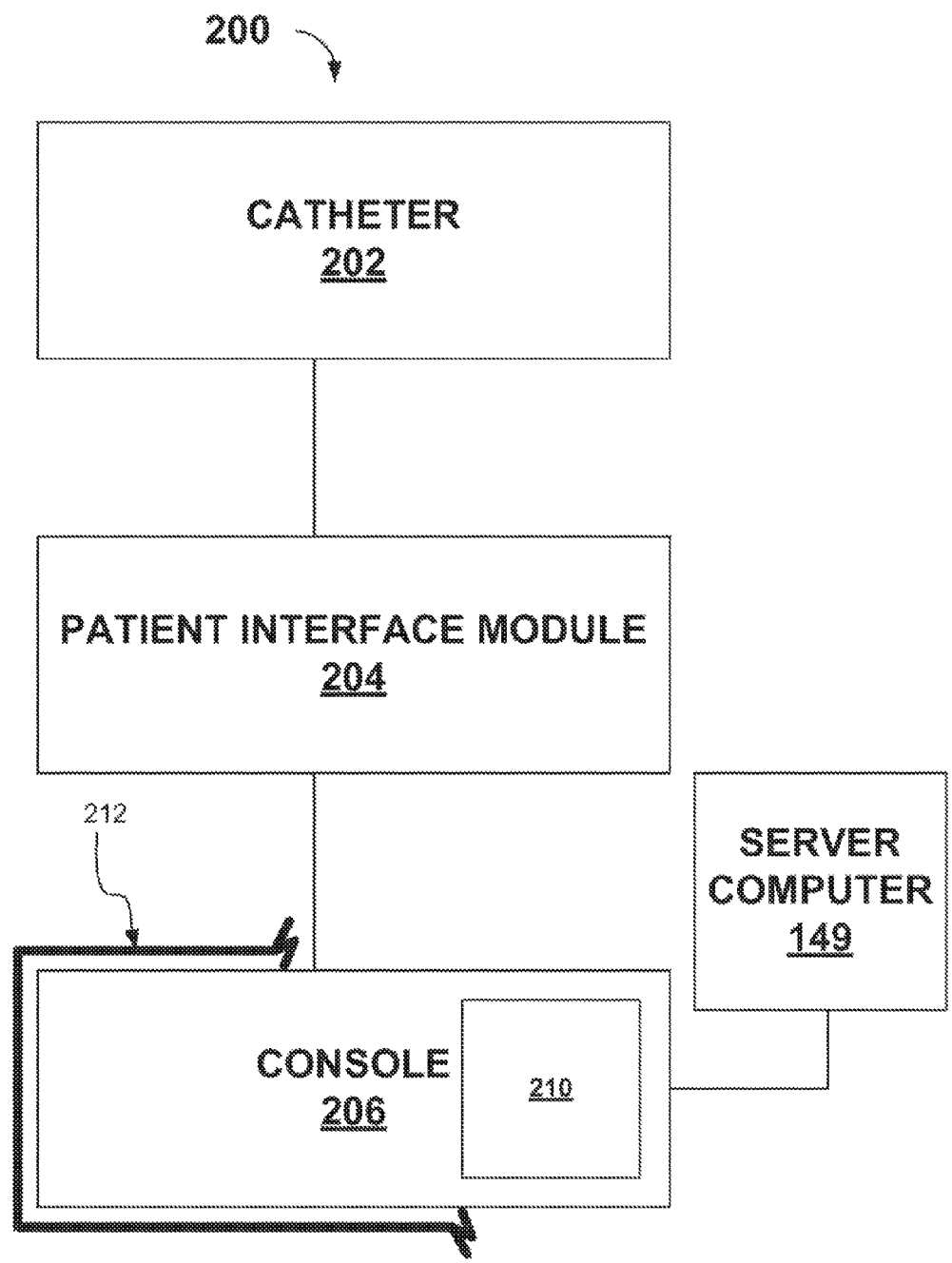
FIG. 2 shows a high-level diagram of an IVUS system and catheter according to an embodiment of the subject matter disclosed herein.

With such a computing environment as described with respect to FIG. 1, an IVUS system having various embodiments as discussed herein may be practiced and used. FIG. 2 shows a high-level block diagram of an intravascular ultrasound catheter system 200 including a catheter 202, a patient interface module 204, and a console 206. The patient interface module 204 may be electrically and mechanically coupled to the catheter 202 such that the catheter may collect raw data about a part of human anatomy and send the raw data to patient interface module 204. The patient interface module 204 may process the incoming data for transmission to a coupled console 206 and further provides electrical isolation of the patient from the system. The patient interface module 204 is described in additional detail in U.S. patent application Ser. No. 12/633,278 by Moore et al, the complete disclosure of which is hereby incorporated by reference.

The patient interface module 204 and console 206 may be communicatively coupled by physical analog and digital signal lines. Such physical couplings may include proprietary cabling, common universal serial bus coupling or other suitable coupling that allows for signal communications and/or power to be provided to the patient interface module 204. In other embodiments, the patient interface module 204 may be powered by a local battery and communicatively coupled to the console 206 through a wireless communication protocol, such as a local Wi-Fi network. Further, the console 206 may be communicatively coupled to a server computer 149 having medical images stored thereon for accessing and downloading. These stored images may represent images captured from a previous deployment of a catheter in a specific area of the human anatomy.

The console 206 may receive processed data from the patient interface module 204 and produce images about the scanned area of human anatomy. The images may generally comprise one or more tomographic images which may be a specific location of a part of a human anatomy. A tomographic image (sometimes called a transverse image) results from a rotating sonic signal emanating from a point source at the end of the catheter and then receiving echo signals that yield data about surroundings in a single plane. As the catheter moves forward (or backward), a tomographic image in a different plane may be derived. Together, the multiple tomographic plane images may then be thought of as a series of tomographic images. If stacked side-by-side (in a pancake-like manner), a longitudinal image may be revealed that represents a three-dimensional image of the human anatomy that was scanned. Further, such a longitudinal image may be "cut" along a cut-plane axis such that a display may show the series of tomographic images from a [particular cut plane.

In conventional systems, the tomographic image and longitudinal image are generally displayed on a non-touch screen. The operator may use a pointing device, such as a touch pad or track ball, to select a different tomographic image or select a different cut-plane for the longitudinal image. The operator can search the sequence of images for the minimum lumen area by repeatedly adjusting the tomographic image and longitudinal image. For example, the operator may use the pointing device to select an on-screen control handle to select a different image or change the longitudinal image cut-plane. The use of a non-touch screen for image display, however, may limit user interaction and effectively increase procedure time. The use of pointing devices may require additional steps, such as hovering a display cursor for a predetermined duration over an on-screen control handle, before the operator can interact with the on-screen control handle. The use of control handles may further impede operator interaction if the control handles are small and located at only a specific screen location. Operator interaction can be still further impeded if the system requires precise proximity of the display cursor to the control handle before the control handle can be activated. Thus, better operational control of the images is desirable.

Thus, in embodiments herein, the console 206 may include a touch screen 210. In this manner, the console 206 may be used to control operation of the patient interface module 204 and the imaging aspect of the catheter 202 through the use of a touch screen 210. The touch screen 210 is configured to detect tactile input when an object comes into contact or is near the touch screen, e.g., engages the touch screen. Further, as the console 206 will be subject to repeated touching, a sterile cover 212 that is interchangeable may be present surrounding the entire console 206.

In an embodiment, the intravascular ultrasound catheter system 200 provides for image guidance of percutaneous coronary interventions such as stent deployment. As such, to further facilitate ease of use by an operator when viewing images, the console 206 includes a touch screen 210 configured for image display and operator interaction as illustrated in FIG. 3.

Figure 3:
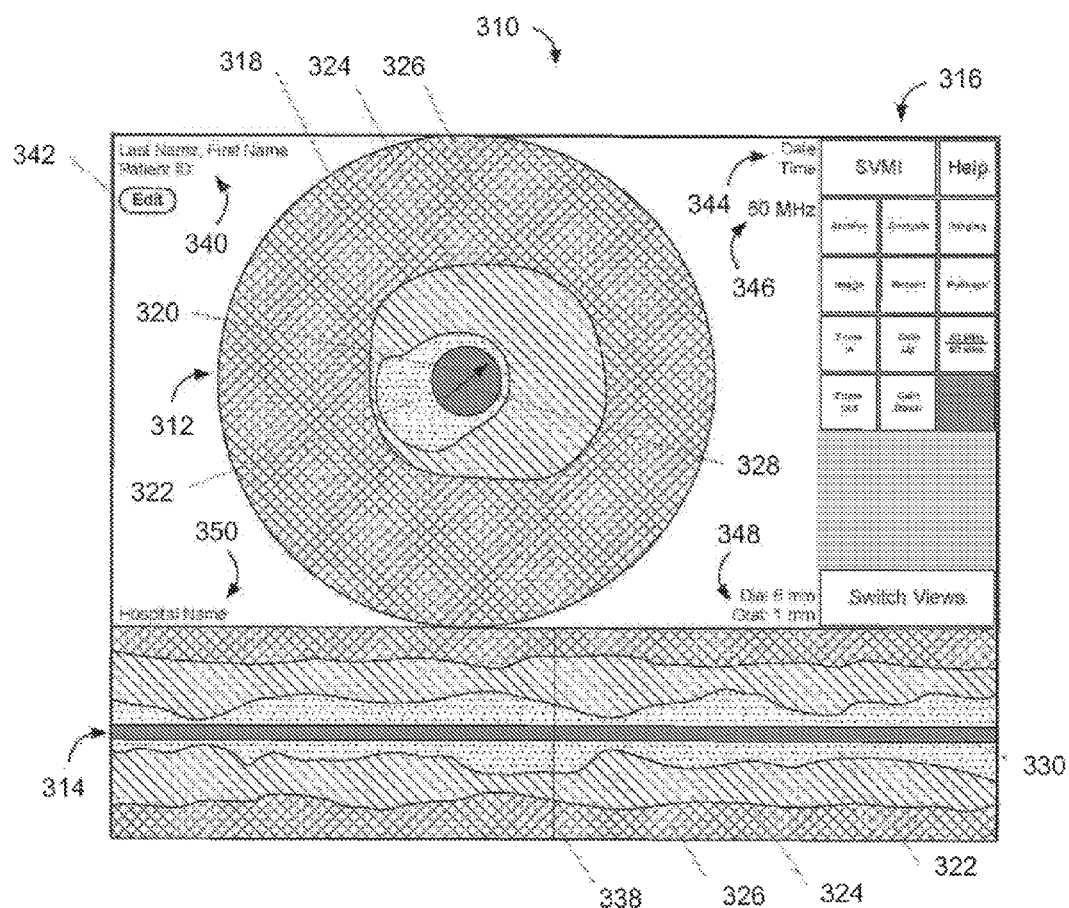
FIG. 3 illustrates an IVUS imaging touch screen including a longitudinal image and tomographic image according to an embodiment of the subject matter disclosed herein.

Referring now to FIG. 3, a view of the touch screen 210 of the console 206 of FIG. 2 is shown during operation with an example image displayed. The touch screen 210 here displays a tomographic image 312, a longitudinal image 314, and common controls 316 for manipulating these images as well as image analysis and archiving. In this embodiment, the tomographic image 312 is a cross-sectional view of a diseased coronary artery. Throughout the remainder of this disclosure, the example of a diseased coronary artery will be used to illustrate the concepts claimed herein, however, a skilled artisan understands that any tomographic image in any medical context may be used with the systems and methods described herein.

The tomographic image is spatially limited to a field of view 318. The tomographic image 312 of the coronary artery may include a catheter mask 320 that identifies catheter location within the diseased coronary artery. The tomographic image 312 also generally includes a coronary artery lumen 322, intimal plaque 324, and surrounding tissue 326 which may include membranous adventitia tissue. The tomographic image 312 may further include a cut-plane indicator 328 to indicate the cut-plane along an axis of the longitudinal image 314.

The longitudinal image 314 is constructed from a cut-plane of a sequence of the tomographic images generally acquired by a catheter 202 and assembled by a program module executing on the console 206. The longitudinal image 314 includes a longitudinal axis in the horizontal direction and a transverse axis in the vertical direction. The longitudinal image 314 further includes a catheter mask 330, the coronary artery lumen 322, intimal plaque 324, and the surrounding tissue 326. The longitudinal image 314 still further includes a longitudinal position indicator 338 to indicate the longitudinal cut-plane position of the tomographic image 312.

In a procedure according to one embodiment, an operator positions the IVUS catheter 202 distal to a coronary artery segment of interest. A sequence of tomographic images of the coronary artery is acquired at different longitudinal positions as the IVUS catheter transducer is translated longitudinally from a distal position to a proximal position. The tomographic image 312 and longitudinal image 314 may be shown in real time and the sequence of images may include many thousands of tomographic images. In an embodiment, the longitudinal image includes a "one pixel-wide" cut-plane for each tomographic image. For a touch screen having a 1280 pixel width, the longitudinal image is limited to showing the cut-plane for at most 1280 tomographic images. For image sequences including more than 1280 tomographic images, a limited section of the longitudinal image 314 can be displayed. Sections of the longitudinal image 314 that are not displayed may be stored in an off-screen buffer. An IVUS system that includes touch movement recognition according to an embodiment enables the operator to intuitively and rapidly search the sequence of images for an area of interest, such as the minimum lumen area. Such operator movements are discussed below with respect to FIGS. 4-6.

Figure 4:
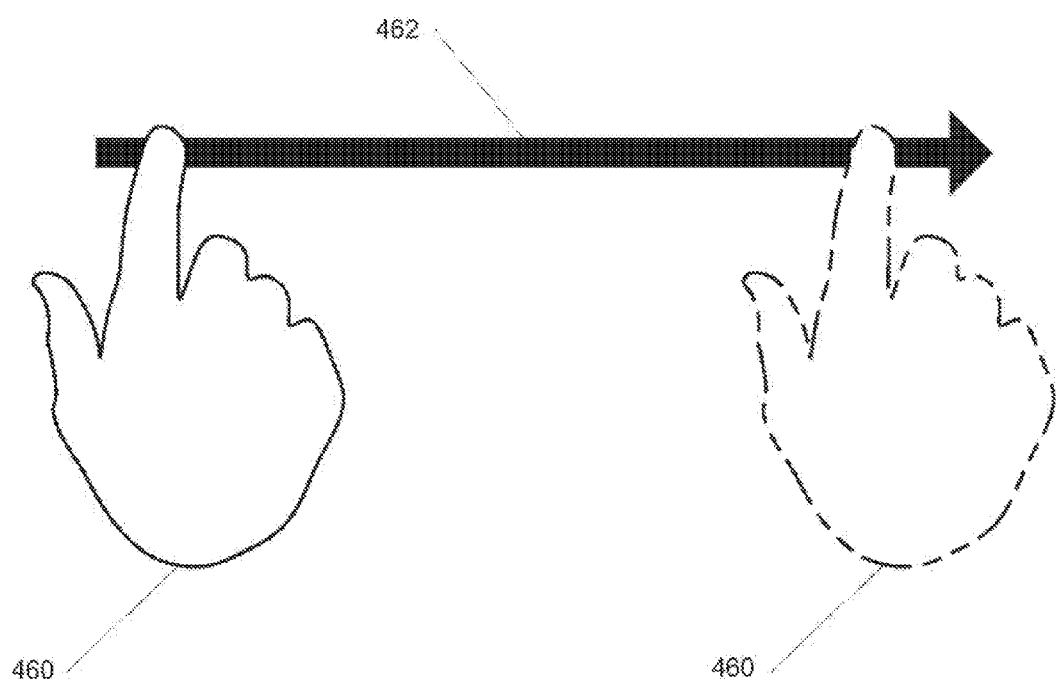
FIG. 4 illustrates a touch movement with an imaging touch screen of FIG. 3 according to an embodiment of the subject matter disclosed herein.

Referring now to FIG. 4, a touch movement is illustrated. In an embodiment, a hand 460 in an initial position is dragged to the right as indicated by arrow 462 in a substantially horizontal direction to a final position where the hand 460 is illustrated in dashed lines. During this touch movement process, the finger of hand 460 is in contact with the touch screen 210. In other embodiments, the hand may include a glove such that only the glove material comes into contact with the touch screen 210. In still other embodiments, an operator may use an instrument, such as a stylus or pen to effect movement detection by the touch screen 210.

Figure 5:
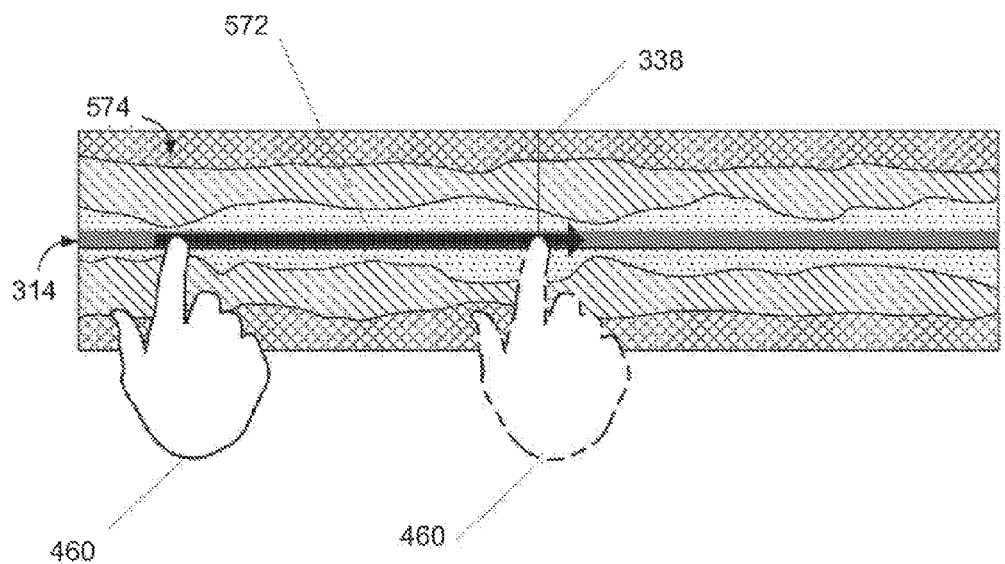
FIG. 5 illustrates a horizontal touch movement on a longitudinal image with an imaging touch screen of FIG. 3 according to an embodiment of the subject matter disclosed herein.

FIG. 5 illustrates a substantially horizontal touch movement that is applied to the longitudinal image 314. In this embodiment the touch movement is initiated at a section of the longitudinal image with a minimum lumen area 574. The finger of hand 460 touches the touch screen 210 at the minimum lumen area 574. The finger of hand 460 then moves across the touch screen 210 in a substantially horizontal direction 572. The finger of hand 460 stops at the longitudinal position indicator 338 and is lifted off the touch screen 210. The substantially horizontal touch movement causes the longitudinal image 314 to pan in the direction of the touch movement.

In one embodiment with a touch screen 210 having a 1280 pixel width, the longitudinal image 314 is updated to include the cut-plane of the 1280 tomographic images having the middle tomographic image centered at the longitudinal position indicator 338. The tomographic image 314 is updated to correspond to the longitudinal position represented by the longitudinal position indicator 338.

Figure 6:
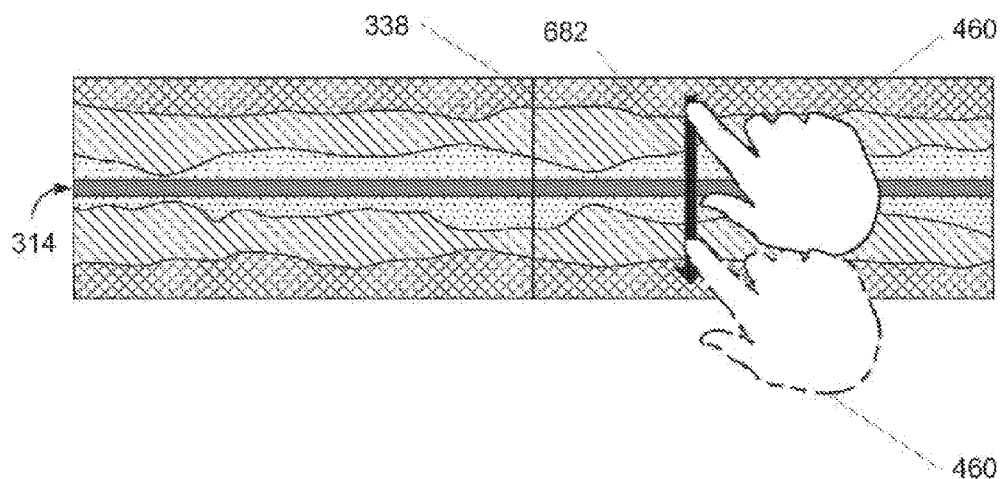
FIG. 6 illustrates a vertical touch movement on a longitudinal image with an imaging touch screen of FIG. 3 according to an embodiment of the subject matter disclosed herein.

FIG. 6 illustrates a substantially vertical touch movement that is applied to the longitudinal image 314. The finger of hand 460 touches the touch screen 210 and then moves across the touch screen in a substantially vertical direction 682. The finger stops as indicated by the hand 460 in dashed lines and is lifted off the touch screen. The substantially vertical touch movement causes the cut-plane of the longitudinal image to rotate. The longitudinal image 314 is updated. The cut-plane indicator 328 as illustrated in FIG. 3 is also updated.

With these touch screen operations and movements available to an operator, one can manipulate a medical image quickly and easily to find specific areas of interest. Such a method for doing so is shown and described with respect to FIG. 7 below which may be implemented as a method in a computing environment in a program module such as a heuristics engine that may be part of the console 206 of FIG. 2.

Figure 7:
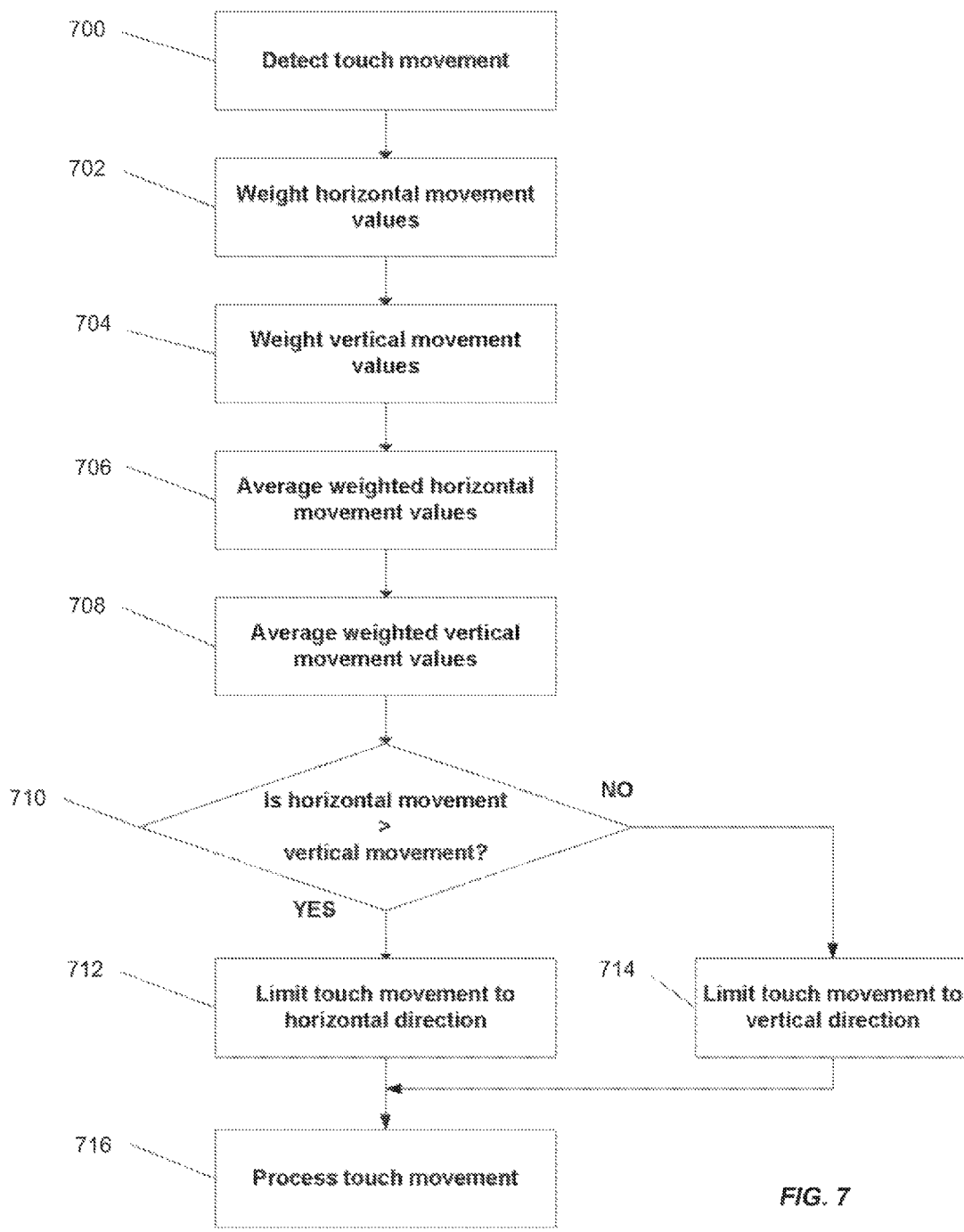
FIG. 7 is a flow diagram illustrating processing stages for a touch movement with an imaging touch screen of FIG. 3 according to an embodiment of the subject matter disclosed herein.

One set of processing steps for processing touch movements on the longitudinal image in accordance with aspects of one embodiment is illustrated in FIG. 7. The process initiates with a touch movement being detected in step 700. One or more horizontal movement values, which may include direction and speed, are weighted in step 702. Further, one or more vertical movement values, which may also include direction and speed, are weighted in step 704. Generally speaking, when a horizontal movement is detected, a selection marker may be moved along a central axis of the longitudinal image and may correspond to one of the sequence of tomographic images that comprise the longitudinal image. Thus, a horizontal movement, in effect, may change the displayed tomographic image. Similarly, if a vertical movement is detected, the entire longitudinal image (i.e., each of the tomographic images) may be rotated about the central axis.

The horizontal movement values can be weighted such that the longitudinal image is preferentially panned by a touch movement. A running average of the weighted horizontal movement values is calculated in step 706 wherein the running average may use the last 10 sets of horizontal movement values. A running average of the weighted vertical movement values is then calculated in step 708 wherein the running average may use the last 10 sets of vertical movement values. In an alternative embodiment, the weighted average may be calculated from a set of data points within a specific time window (for example, 100 ms) that may include a suitable number of movement values. The set of averaged, weighted horizontal movement values is then compared to the set of averaged, weighted vertical movement values in step 710. If the horizontal movement is considered greater than the vertical movement, the touch movement is limited to the horizontal direction in step 712. If the vertical movement is considered greater than the horizontal movement, the touch movement is limited to the vertical direction in step 714. The touch movement is then processed in step 716. Here, the horizontal movement results in a pan of the longitudinal image and a vertical movement results in a cut-plane rotation of the longitudinal image. Touch movements can be processed in a repeated manner.

In another aspect of various embodiments, the IVUS imaging system may be used to acquire a sequence of tomographic images of a coronary artery. The touch screen displays at least one of images in the sequence of tomographic images. The touch screen further displays at least one longitudinal image, wherein the longitudinal image represents a cut-plane of the sequence of tomographic images. A further aspect of various embodiments is a method to search the sequence of images to identify at least one image feature of interest. An image feature of interest may be a minimum lumen area. The image search methods may involve the use of touch movements applied to regions of the touch screen wherein the longitudinal image is shown. Touch movements in the longitudinal direction of the longitudinal image may be processed to pan the longitudinal image. Touch movements in the transverse direction of the longitudinal image may be processed to rotate the cut-plane of the longitudinal image. Yet another aspect of various embodiments is touch movement processing to enable either longitudinal image panning or longitudinal image cut-plane rotation for a discrete touch movement, but not simultaneous panning and rotation. Touch movement processing provides a preference for longitudinal image panning.

While the subject matter discussed herein is susceptible to various modifications and alternative constructions, certain illustrated embodiments thereof are shown in the drawings and have been described above in detail. It should be understood, however, that there is no intention to limit the claims to the specific forms disclosed, but on the contrary, the intention is to cover all modifications, alternative constructions, and equivalents falling within the spirit and scope of the claims.

What is claimed is:

1. An intravascular ultrasound system, comprising:
a catheter configured to produce data;
an interface module coupled to the catheter and configured to receive the data; and
a console having a display with a touch screen coupled to the interface module, the console being configured to:
produce a sequence of tomographic images from the data acquired by the catheter,
display at least a first image produced from the sequence of tomographic images on the display, the sequence of tomographic images combinable to form a three-dimensional image of an object, the three-dimensional image having a longitudinal axis extending therethrough, the first image representing a first cut-plane view at a cut-plane of the three-dimensional image, the cut-plane containing the longitudinal axis,
display a cut-plane indicator on the display to indicate a first rotational orientation of the cut-plane corresponding to the first cut-plane view shown in the first image,
receive a tactile input and determine a primary direction of movement of an object engaging the touch screen using at least one heuristic, the at least one heuristic comprises a first vertical screen scrolling heuristic for determining the primary direction of movement of the object engaging the touch screen, manipulate at least the first image based on the determined primary direction, the manipulation comprises rotating the orientation of the cut-plane to a second rotational orientation about the longitudinal axis in response to the first vertical screen scrolling heuristic, the first vertical screen scrolling heuristic being oriented in a direction perpendicular to the longitudinal axis, update the display to display a second image corresponding to a second cut-plane view of the three-dimensional image taken at the second rotational orientation of the cut-plane, update the display to display the cut-plane indicator oriented at the second rotational orientation at which the second image is taken.

2. The intravascular ultrasound system of claim 1 wherein the console is further configured to display a longitudinal image corresponding to a plurality of tomographic images.

3. The intravascular ultrasound system of claim 1, further comprising a heuristic decision engine configured to analyze the tactile input and to manipulate at least one image from the sequence of tomographic images in only one direction.

4. The intravascular ultrasound system of claim 3, wherein the heuristic decision engine further comprises:
a horizontal screen scrolling heuristic for determining that the tactile input corresponds to a one-dimensional horizontal panning command for the sequence of tomographic images; and
a second vertical screen scrolling heuristic for determining that the tactile input corresponds to a one-dimensional vertical panning command for the sequence of tomographic images.

5. The intravascular ultrasound system of claim 1, wherein the display further comprises a sterile cover.

6. The intravascular ultrasound system of claim 1, wherein the tactile input from the object engaging the touch screen further comprises tactile input from a hand.

7. The intravascular ultrasound system of claim 1, wherein the tactile input from the object engaging the touch screen further comprises tactile input from a gloved hand.

8. The intravascular ultrasound system of claim 1, wherein the tactile input from the object engaging the touch screen further comprises tactile input from a stylus.

9. An intravascular ultrasound system, comprising:
a catheter configured to produce data;
an interface module coupled to the catheter and configured to receive the data; and
a console, comprising
a display with a touch screen coupled to the interface module, the touch screen being configured to receive a tactile input, and
a decision engine configured to process detected tactile inputs on the touch screen, the decision engine further configured to:
determine a running average of detected horizontal movements based on either one of a predetermined number of previous horizontal movements or a set of horizontal movements within a specific time window;
determine a running average of detected vertical movements based on either one of a predetermined number of previous vertical movements or a set of vertical movements within a specific time window;
repeatedly determine which running average is higher:
if the running average of the horizontal movements is higher, then change a first image displayed on the display; and
if the running average of the vertical movements is higher, then rotate a cut-plane of a second image displayed on the display, the second image produced from a sequence of tomographic images that are combinable to form a three-dimensional image, the three-dimensional image having a longitudinal axis extending therethrough, the second image representing a cut-plane view at a cut-plane of the three-dimensional image, the cut-plane containing the longitudinal axis.

10. The intravascular ultrasound system of claim 9, wherein the displayed image is an image of a coronary artery.

11. The intravascular ultrasound system of claim 9, wherein the displayed image is a tomographic image of a portion of human anatomy.

12. The intravascular ultrasound system of claim 9, wherein the console comprises a communication module configured to receive a sequence of images, the sequence of images received from a coupled catheter.

13. The intravascular ultrasound system of claim 12, wherein the sequence of images are received from a communicatively coupled server computer.

14. The intravascular ultrasound system of claim 9, wherein the running average of detected horizontal movements is a weighted average of horizontal movements and the running average of detected vertical movements is a weighted average of vertical movements.

15. An intravascular ultrasound system, comprising:
a catheter configured to produce data;
an interface module coupled to the catheter and configured to receive the data; and
a console having a display with a touch screen coupled to the interface module, the console being configured to:
provide image data from a sequence of tomographic images of an object, the sequence of tomographic images combinable to form a three-dimensional image of the object, the three-dimensional image having a longitudinal axis extending therethrough,
display, on the display, a longitudinal sectional image of the three-dimensional image taken along a cut-plane of the three-dimensional image, the cut-plane containing the longitudinal axis,
display a selection marker on the longitudinal sectional image at a point along the longitudinal axis,
display, on the display, near the longitudinal image, a cross-sectional image of the three-dimensional image taken at a plane normal to the longitudinal axis and taken at the point on the longitudinal axis corresponding to the location of the selection marker,
detect a tactile input on the display corresponding to a horizontal movement,
in response to the tactile input corresponding to the horizontal movement, move the selection marker proportional to the detected horizontal movement to a new position along the longitudinal axis relative to the longitudinal image,
update the display to display a second cross-sectional image of the three-dimensional image taken at a plane normal to the longitudinal axis and taken at a new point on the longitudinal axis corresponding to the new location of the selection marker, display the new location of the selection marker on the display, detect a tactile input on the display corresponding to a vertical movement, in response to the tactile input corresponding to the vertical movement, rotate the orientation of the cut-plane to a new rotational orientation, the rotation being proportional to the detected vertical movement about the longitudinal axis in response to the vertical movement, the vertical movement being oriented in a direction generally perpendicular to the longitudinal axis, update the display to display, on the display, a second longitudinal sectional image of the three-dimensional image taken along the rotated cut-plane, and display the cut-plane oriented at the new rotational orientation.

16. The intravascular ultrasound system of claim 15, wherein the console is configured to determine whether the vertical movement or the horizontal movement is more prominent, and disregard a less prominent movement.

17. The intravascular ultrasound system of claim 16, wherein the console is configured to calculate a lumen area corresponding to the displayed tomographic image.

18. The intravascular ultrasound system of claim 16, wherein the console is configured to determine a lumen area for each tomographic image and display the tomographic image corresponding to the lowest lumen area calculated.

19. The intravascular ultrasound system of claim 16, wherein the console is configured to receive the sequence of tomographic images from the data produced by the catheter.

20. The intravascular ultrasound system of claim 16, further comprising a server computer coupled to the display, wherein the console is configured to the sequence of tomographic images from the server computer.

* * * * *